United States Patent [19]

Taylor et al.

[11] Patent Number: 5,125,730
[45] Date of Patent: Jun. 30, 1992

[54] PORTABLE DYNAMIC FUNDUS INSTRUMENT

[75] Inventors: Gerald R. Taylor, Dickinson, Tex.; Richard T. Meehan, Aurora, Colo.; Norwood R. Hunter; Michael P. Caputo, both of Friendswood, Tex.; C. Robert Gibson, Houston, Tex.

[73] Assignee: The United States of America as represented by the Administrator of the National Aeronautics and Space Administration, Washington, D.C.

[21] Appl. No.: 562,095

[22] Filed: Jun. 29, 1990

[51] Int. Cl.⁵ .............................................. A61B 3/14;
[52] U.S. Cl. ................................... 351/206; 351/221
[58] Field of Search ............... 351/206, 214, 221, 246; 354/62

[56] References Cited

U.S. PATENT DOCUMENTS

| | | | |
|---|---|---|---|
| 4,699,482 | 10/1987 | Utsugi | 351/206 |
| 4,755,043 | 7/1988 | Carter | 351/205 |
| 4,848,897 | 7/1989 | Aizu et al. | 351/221 |
| 4,993,827 | 2/1991 | Benedek et al. | 351/221 |

*Primary Examiner*—Paul M. Dzierzynski
*Attorney, Agent, or Firm*—Russell E. Schlorff; Guy M. Miller; Edward K. Fein

[57] ABSTRACT

A portable diagnostic image analysis instrument for retinal funduscopy in which an eye fundus image is optically processed by a lens system (24) to a CCD device (32) which produces recordable and viewable output data and is simultaneously viewable on an electronic view finder 36. The fundus image is processed to develop a representation of the vessel or vessels from the output data.

2 Claims, 3 Drawing Sheets

PORTABLE DYNAMIC FUNDUS INSTRUMENT

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

FIELD OF THE INVENTION

This invention relates to a portable diagnostic image analysis instrument for retinal funduscopy, and more particularly to a portable dynamic fundus instrument for obtaining dynamic retinal information from an eye with contemporaneous visual display and data recording.

BACKGROUND OF THE INVENTION

Fundus cameras, such as the commercially available "Kowa RC-2 Camera" have been available for some time and are available as portable hand held units which are adapted to produce either a 35 mm photo or a polaroid photo of the fundus of the eye. The Kowa RC-2 Camera can be used for Otorhinolargngology, Gynecology, Dentistry, Dermatology and Surgery. In all instances, the camera obtains a photo which depicts a physical condition at the instant of time of the photographic exposure. In fluorescein angiography, the camera can be used to obtain a series of black and white slides during an injection of fluorescein over a period of time. As is obvious, there is a time delay between the taking of a picture and its development; the photo depicts only a static condition; and the inspection of the eye for a period of time is limited to the operator for the period of time.

Retinal funduscopy has enjoyed widespread use in ophthalmology for the diagnosis and monitoring of ocular disease and effects of therapy with the use of color, black and white, stereo and fluorescein angiography images which are routinely obtained with 35 mm or polaroid cameras. However, limitations of these cameras include the expense, extensive training of personnel in photographic principles, costs in film developing, delay in obtaining information (or knowledge that a quality image was obtained). Also, the flash intensity required for photographic film of patients with ocular pathlogy (cataracts, inflammation, scaring, or hemorrhage in the anterior or posterior chamber) is difficult because the intense light of the flash reflects and therefore obscures the retina or degrades the image quality.

In some instances, video images are reputed to be obtained from large table top systems and use of digital technology. An expensive retinal imaging system which employs a laser (Scanning Laser Ophthalmoscopy) as the illumination light source is available. There are currently, however, no low cost, portable systems commercially available which incorporate video imaging with digital image analysis in retinal funduscopy.

PATENT ART

U.S. Pat. No. 4,848,897, dated Jul. 18, 1989, (Class 351/221) describes an ophthalmological diagnosis processing apparatus to measure blood flow state in tissue of the eye fundus (section 10, line 11-12). This system uses laser illumination to produce laser speckling of the blood vessel. The resulting speckle photons are counted to measure blood flow velocities. The Portable/Bedside Retinal Digital Image Analysis System of the present invention is not a laser based system. The illumination source is a 10 watt incandescent bulb. The system does not measure blood flow velocities but rather measures blood vessel diameters.

U.S. Pat. No. 4,755,043, dated Jul. 5, 1988, (Class 351/205) describes a portable scanning digital pupillometer and method of use. The device and methods are specifically related to the measurement in the size of an eye pupil (section 6, line 30-31). The device uses an infrared light source and does not resolve or quantify the blood vessels within the eye. The Portable/Bedside Retinal Digital Image Analysis System of the present invention is used in imaging and measuring in the area of the human eye retina.

U.S. Pat. No. 4,699,482, dated Oct. 13, 1987, (Class 351/206) describes an ophthalmoscope that incorporates the use of a fiber optic bundle to illuminate and image the eye retina. The description of the system relies heavily on the fiber optic illumination and imaging cable (section 6, line 48-61). Several components of the system, including hardware, are not specified. A fiber optic device similar to U.S. Pat. No. 4,699,482 was used on STS-34 to image the retina. The resulting images had a narrow field of view and required a very bright illumination source. The system described in U.S. Pat. No. 4,699,482 can use an incandescent illumination lamp with a luminous intensity of 30-50 watts (section 2, line 21-22). This is an extremely bright source that can cause subject discomfort and pain. The Portable/Bedside Retinal Digital Image Analysis System of the present invention does not incorporate the use of fiber optics. The illumination and imaging system uses conventional optical lenses with a single light source. The Portable/Bedside Retinal Digital Image Analysis System of the present invention uses a 10 watt or lower incandescent bulb and can therefor be categorized a low light level intensity retinal imaging system. The Ophthalmic System of the patent also uses fiber optic bundles of 1-5 meters (section 6, line 23) or greater in length to interface with the image receiver. The Ophthalmic System description does not mention portability or digital analysis of the images. The system of the present invention is small, hand-held, and portable. All the components needed to view the image are held in the operator's hand.

SUMMARY OF THE PRESENT INVENTION

Clinicians and investigators have long recognized that the retinal vascular system of an individual reacts to various systemic disorders in the body. For example, vascular changes associated with hypobaric hypoxia, cerebral edema, vasculitis, or malignant hypertension can be detected in the retinal vascular system and are usually reversible without treatment. This invention concerns itself providing a diagnostic instrument and method for ascertaining and recording the dynamic conditions of the retinal vascular system so that the diameter and length of blood vessels can be ascertained and evaluated to facilitate treatment of systemic disorders and so that responses to such treatment can be properly determined.

The present invention is footed on the ability to read and display changes in the caliber (diameter) over a length of retinal vessel (arteries and veins) over a period of time.

The present invention has application in NASA/Space Station and Shuttle-Medical diagnostic and investigation use. It is useful in aviation medicine for monitoring crew ocular parameters during centrifuge tests or cockpits (G-induced loss of consciousness). The fact that each individual eye (like a fingerprint) has unique characteristics creates a security application to document individual identity by retinal vascular patterns. In military medicine (field hospitals, submarines, etc.) the invention can be used to detect and monitor ocular or CNS pathology which may require evacuation or referral for treatment by an ophthalmologist or neurosurgeon. In remote locations, examples: off shore oil drilling rigs, expeditions, polar regions/expeditions/mountaineering environments, the invention can be used to relay data to a diagnostic center.

In general, this invention is specifically designed to function as a light weight, portable, inexpensive medical and investigative instrument for the detection, monitoring and objective quantification of ocular/systemic disease or physiologic alterations of the retinal vessels or structures in the anterior and posterior chamber. The invention can function with the subject (human or animal) in any position, during different gravitational fields and in novel environments (chambers, operation rooms, space vehicles, centrifuges, aircraft, etc.) and can provide images which can be directly digitized or visualized and analyzed in remote locations. This device can also be fitted with adaptors so that images (stereo and magnification) can be obtained to facilitate detecting lesions or disease states from the skin, nose, ear, throat and oral cavities.

DESCRIPTION OF THE PRESENT INVENTION

Figure 1:
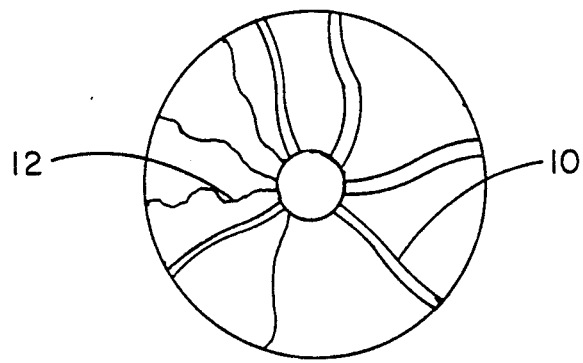
FIG. 1 is a schematic representation of the fundus of an eye to show arteries and veins.

With reference to FIG. 1, a representation of a view of the bottom or back surface (fundus) of an eye and depicts the blood vessels of arteries 10 and veins 12. Both the arteries and veins have a length, caliber, and tortuosity (various curvatures) which are unique to each person. Blood is transmitted through the vessels by the heart action and the vessel configuration in terms of caliber and tortuosity is a function of several body systems. Since the caliber and tortuosity are a dynamic function of the heart action, still photographic pictures are not definitive of the dynamic conditions occurring in the vessels.

In perfecting the present invention it was necessary to first establish that the caliber of retinal vessels could be quantified with sufficient precision with a digital image analysis system. This was accomplished by obtaining color retinal photographs with a hand-held Kowa RC-2 fundus camera using 35 mm Ektachrome 64 film. Black and white images were obtained with a Topcon TRE-FE fundus camera and Polaroid HC film. The hand-held camera was stabilized against the subject's zygomatic arch or forehead.

The photographic slides were placed on a fluorescent light box and digitized with a Dage-MTI digitizing camera (Michigan City, Id.) and the focal length and lens remained unchanged between different images for each study. The digitized images were processed and displayed on a PSICOM 326 digital imaging system (Perceptive Systems, Inc., Houston, Tex.) at the NASA/Johnson Space Center. The contrast between edges of vessels and the retina was maximized by adjusting the gray-level density scale. The beginning and end of each vessel segment to be analyzed was selected by the operator using a trackball-controlled cursor. The segment between the optic disc and the first major bifurcation of the largest and best-resolved arteries and veins was selected. An available vessel-tracking program was utilized to identify the edges of vessels and displayed the mean width of vessels in pixels. The mean width for each vessel segment was reported to the nearest 0.01 of a pixel. This measurement of vessel width was derived by the computer after averaging hundreds of separate measurements which were obtained perpendicular to the vessel midline between both edges of the vessel along the entire vessel segment length one pixel at a time.

Results were reported as group means $\pm$SE or as percentage changed from baseline values. Data were entered into the Clinical Research Center's Clinfo computer (Bolt, Beranek, and Newman, Inc., Cambridge, Mass.) at the University of Texas Medical Branch. Normally distributed data were analyzed by analysis of variance (ANOVA) with repeated measures. The Wilcoxon signed ranks test was used for data not normally distributed (BMDP) Statistical Software, Inc., Los Angeles, Calif). Results with P values $<0.05$ were considered significant.

Having established that vessel edges (diameter) could be determined from digitized data with sufficient accuracy, an analysis was made in different environments, i.e., retinal images of subjects during exposure to hypobaric hypoxia, to 48 hours of 10° head-down tilt, and to brief weightlessness conditions provided by parabolic flight. This was to establish the viability of diameter measurements relative to different environment or conditions.

The first hypoxia experiment involved photographing the right and left ocular fundi of seven subjects at sea level, and at simulated altitudes of 10,000, 17,500, and 25,000 ft (3048, 5334, and 7620 m) inside a decompression chamber with the Topcon camera during a six-week simulated ascent to 29,000 ft (8,839 m) (Operation Everest). The second hypoxia study was performed at 14,110 ft (4300 m) at the U.S. Army Research Institute of Environmental Medicine, Altitude Research Division Facility on Pikes Peak, Colo. Images of the right eye in nine subjects were obtained with the hand-held camera at sea level (Natick, Mass.) and after residing 4 and 17 days on the summit of Pikes Peak in Colorado.

The experimental protocols of head-down tilt and parabolic fight involved use of the hand-held camera powered by a light-weight unit (KRUG International, Houston, Tex.) consisting of four alkaline batteries built to meet safety and performance specifications for flight on board the U.S. Space Shuttle. Images were also obtained from the right eye of nine men between 4:00 P.M. and 6:00 P.M. while they were seated (baseline), and after 10 minutes and 24 and 48 hours of continuous 10° head-down tilt. Swimming goggles were modified by removing the plastic cup to prevent the camera's illumination prism from inadvertently touching the cornea. Simultaneous intraocular pressures were obtained with a pneumotonometer after the cornea was anesthetized with 1 to 2 drops of 0.5% proparacaine hydrochloride (E.R. Squibb, Princeton, N.J.).

The camera was secured by a Bogen arm clamped onto a vertical pole on board the NASA/Johnson Space Center KC-135 aircraft. Images were easily obtained with this system during parabolic flight, but because only one subject was photographed, statistical analyses of diameters of retinal vessels obtained at 1 g vs microgravity conditions were not performed.

Results of multiple measurements of widths of retinal arteries and veins from the same retinal image that was digitized and analyzed on ten separate occasions is shown in Table 1 below.

TABLE 1

Mean Values (±SE) of Repeated Measurements of Multiple Retinal Vessel Widths on Ten Separate Occasions

| Artery | Width pixels | CV %* | Vein | Width pixels | CV % |
|---|---|---|---|---|---|
| 1 | 8.19 (0.02) | 0.7 | 1 | 9.09 (0.04) | 1.5 |
| 2 | 8.36 (0.07) | 2.6 | 2 | 9.53 (0.05) | 1.7 |
| 3 | 9.83 (0.16) | 5.1 | 3 | 10.65 (0.06) | 1.9 |
| 4 | 10.53 (0.05) | 5.1 | 4 | 12.53 (0.26) | 6.7 |
|  | Mean = | 2.5 |  | Mean = | 2.9 |

*CV indicates coefficient of variation

The CVs ranged between 0.7% and 6.7%. The vessel segments from the single best-resolved artery and vein were analyzed because the vessels with the greatest contrast between their edges and surrounding retina are more accurately tracked and measured.

Widths of vessels were next measured on 11 separate retinal photographs from a single subject to determine variations associated with obtaining multiple images from the same person with the hand-held camera. The results in Table 2 below indicate that images obtained can be digitized with a minimum of magnification artifact because, although the camera was hand held, the CV for the optic disc diameter was only 1.5%.

TABLE 2

Mean Values (±SE) of Digital Image Analysis of Vessel Widths of 11 Separate Retinal Images from the Same Subject

|  | Width pixels | CV %* |
|---|---|---|
| Artery | 6.99 (0.09) | 4 |
| Vein | 8.00 (0.07) | 3 |
| Optic disc diameter | 82.36 (1.37) | 1.5 |

*CV indicates coefficient of variation

The mean CVs of optic disc diameters measured on three consecutive days from ten men are shown in Table 3 below. The variance of diameters was no greater when images were obtained with the hand-held camera than when the head and camera were stabilized. Therefore, it was established that accurate analysis of repeated retinal photographs can be performed with a hand-held camera.

TABLE 3

Mean Values (±SE) of Coefficient of Variations (CV) of Optic Disc Diameter Measurements (in Pixels) from Three Consecutive Daily Retinal Images Obtained with the Kowa RC-2 Camera Hand-Held vs Stabilized with the Subject's Head Restrained

| Subject No. | Hand-Held Camera | | Stabilized Camera | |
|---|---|---|---|---|
|  | Optic Disc Diameter | CV % | Optic Disc Diameter | CV % |
| 1 | 89.0 (2.1) | 4 | 87.6 (0.9) | 2 |
| 2 | 99.3 (0.7) | 1 | 106.6 (3.9) | 6 |
| 3 | 86.6 (1.5) | 3 | 87.3 (0.4) | 1 |
| 4 | 101.0 (2.7) | 5 | 94.3 (1.2) | 2 |
| 5 | 102.0 (2.1) | 3 | 101.7 (0.7) | 1 |
| 6 | 109.0 (0.6) | 1 | 107.0 (1.5) | 2 |
| 7 | 99.7 (1.8) | 3 | 98.3 (2.3) | 4 |
| 8 | 93.6 (1.5) | 3 | 90.5 (0.4) | 1 |
| 9 | 105.0 (2.1) | 3 | 104.3 (2.2) | 4 |
| 10 | 83.0 (1.2) | 2 | 87.0 (2.9) | 2.9 |
|  | Mean = | 2.8 | Mean = | 2.9 |

Figure 3:
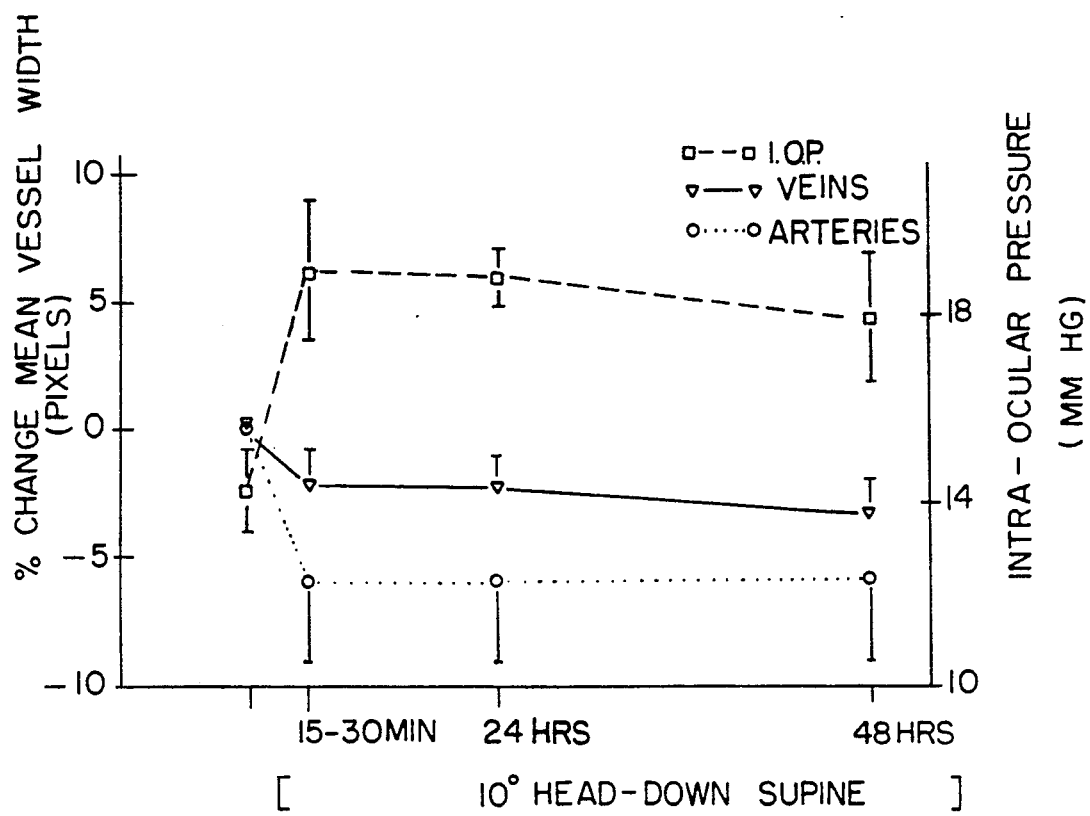
FIG. 3 is a plot of arteries and veins studies under certain conditions.
Figure 2A:
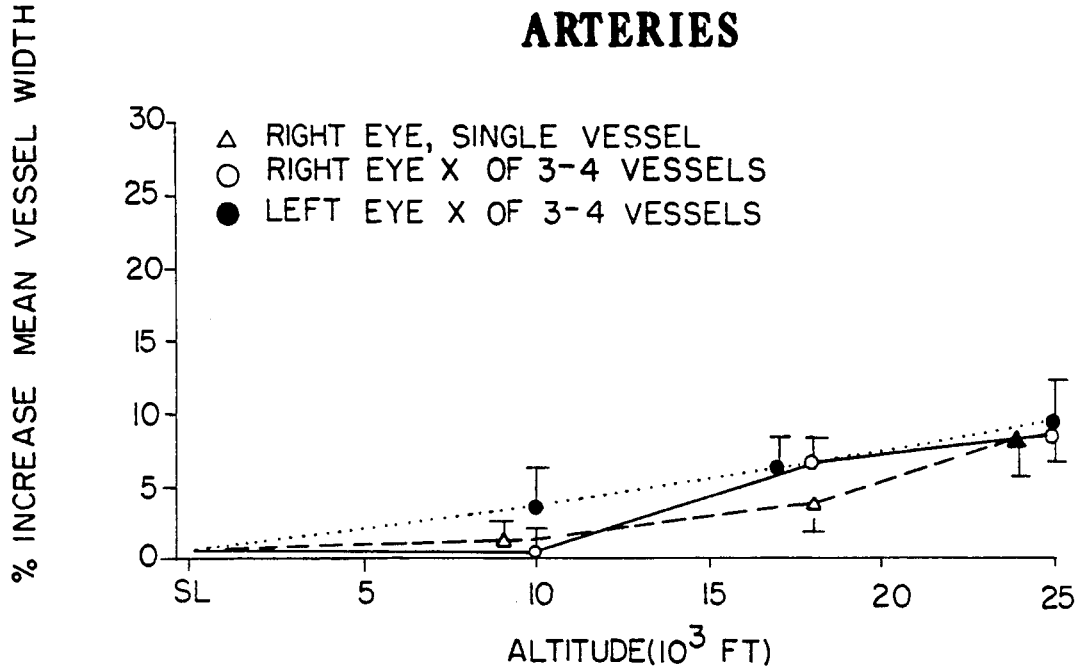
FIGS. 2A and 2B are respectively plots of artery and vein vessel studies.
Figure 2B:
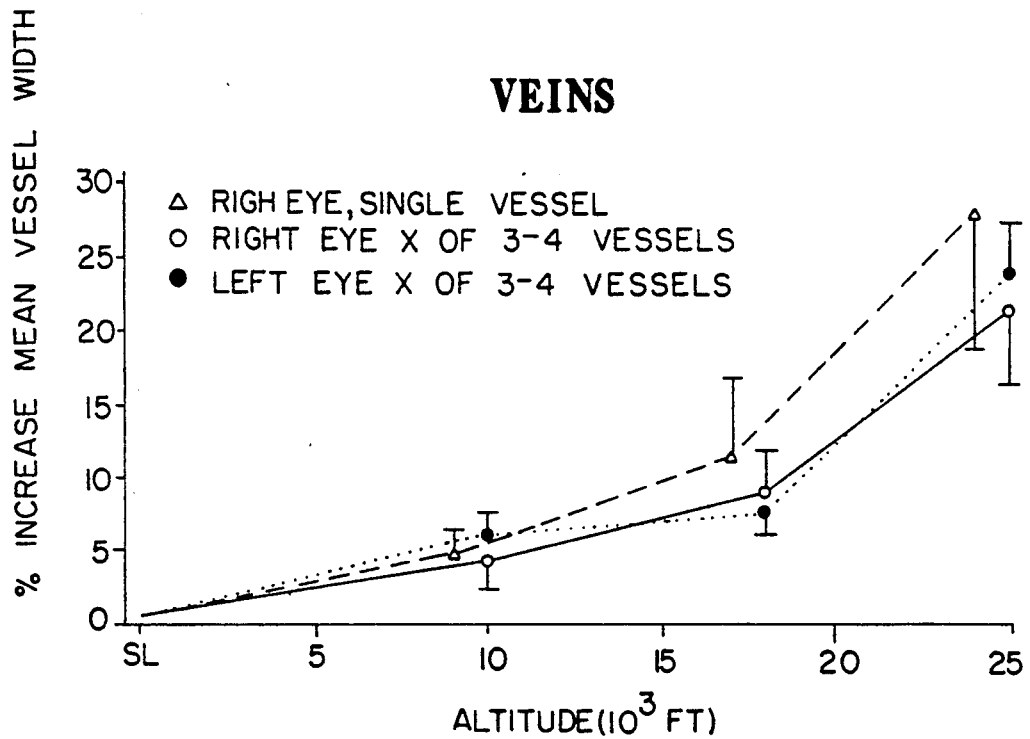

The results presented in FIGS. 2A and 2B indicate that a gradual four-week ascent from sea level to 25,000 ft. induces progressive dilatation of both arteries and veins. The reliability of this method of analysis is demonstrated by comparable results obtained from multiple vessels from either eye or analysis of a single vessel. Furthermore, digital image analysis of widths of retinal vessels is sensitive enough to show that veins apparently dilate progressively more than do arteries at altitudes above 10,000 ft. Ophthalmoscopic examination of both eyes revealed that all subjects had at least one retinal hemorrhage at 25,000 ft. Similar results were obtained when widths of retinal vessels were measured after 4 and 17 days of residence at 14,110 ft. by nine other subjects. The increase in vein widths of 4% ($9.2 \pm 0.1$ vs. $9.6 \pm 0.1$ pixels, $P < 0.01$) and 11% ($9.2 \pm 0.1$ vs. $10.2 \pm 0.1$ pixels, $P < 0.001$) compared with sea level valued was detected after 4 and 17 days of exposure to 14,110 ft., respectively. A significant increase in artery widths of 7% ($7.9 \pm 0.2$ vs. $8.4 \pm 0.3$ pixels, $P < 0.05$), however, was only observed after 17 days at altitude compared with sea-level values. No correlations between the magnitude of retinal vascular dilatation and the severity of acute mountain sickness symptoms was observed The data represented in FIG. 3 shows that the width of both arteries and veins was narrowed after the subjects were placed in the 10° head-down supine position for 10 to 15 minutes ($P < 0.05$). Widths of retinal vessels did not return to baseline values while subjects remained in this position for 24 and 48 hours.

The foregoing examples show that conditions that cause temporary changes in the retinal circulatory system usually do so by increasing or decreasing blood flow in the retinal vessels or by influencing auto-regulation of vessels. Prior studies have documented that changes in the diameter of retinal vessels are associated with changes in retinal blood flow during hypoxia and a characteristic retinopathy at high altitude has been well documented. An ability to non-invasively measure changes in blood flow to the retina in novel environments and clinical situations will greatly facilitate an understanding of the control of retinal vessel physiology and blood flow.

The usefulness of a retinal imaging system in diverse environments not only demonstrates flexibility but also provided corroborative evidence that the system could detect physiologic alterations in blood flow or widths in retinal vessels. The observation that veins progressively dilate more than do arteries at altitude above 14,110 ft. is consistent with the hypothesis that retinal vessels may reflect hypoxia-induced subclinical cerebral edema. However, alterations in retinal vessel auto-regulation from hypoxia per se may have been the cause of these vascular changes because the vessels remained dilated despite the subject's continued residence on the summit of Pikes Peak (14,110 ft.).

The head-down bed-rest study was performed because it is a commonly used model to simulate the well-documented cephalad fluid shifts that occur during orbital space flight in the absence of the normal hydrostatic pressure gradient toward the feet on Earth. It was observed that even during a 10° head-down position there was a narrowing of retinal vessels which may have been a manifestation of the vascular response to the 33% rise in intra-ocular pressure. Researchers have noted reduced retinal arteriole calibers during inversion studies and have hypothesized that this change was due to retinal vascular auto-regulation that acts to maintain constant retinal perfusion despite increases in retinal artery pressure.

The technique described in this application is also directly applicable to clinical ophthalmology. Changes in the caliber of retinal vessels over time are important manifestation of many retinal diseases including, central retinal vein obstruction, hyperviscosity syndrome, diabetic retinopathy, and retinopathy of prematurity. Ophthalmologists currently use ophthalmoscope, fluorescein angiography and projected color transparencies to follow vascular changes. Although these time-honored methods are valuable, they lack precision and may be influenced by subjective bias. However, color transparencies and fluorescein angiograms can be followed in the quantitative fashion described herein and provide objective information upon which clinical decisions can be based.

In the present invention, analysis of vessel images is accomplished by digital image processing. The retinal image is scanned using discrete sampling points (pixels). Each pixel is quantified for brightness at that point. This brightness information is then converted into digital values so that the image can be displayed on a video monitor. Editing functions can be performed to enhance the resolution of the image definition and facilitate analysis of the image to determine the expanded and contracted diameter at the time of the analysis. Because many imaging techniques are available to improve resolution of objects (e.g. contrast/spatial enhancement, histogram stretching, contouring and/or false color representation) the digitizing of vessel images is ideal for resolving and quantifying the small curvilinear retinal vessels.

The advantage of determining vessel widths with a scanning program is that the entire vessel segment is analyzed under dynamic conditions. This greatly reduces the subjective bias and sampling errors associated with attempting to select the identical location along a vessel for diameter measurements between successive still picture images. The other major advantage of this system is the use of a non-subjective method of defining the vessel edges upon which diameter is based. The vessel edges are determined by the changes in the gray level values between the vessel edge and the surrounding retina. The sensitivity of detecting changes in the maximum and minimum caliber of vessels can be increased by including as a correction factor, the optic disc diameter measurement (Table 3). This value corrects for image magnification artifacts due to differences in photographic technique between successive images.

This retinal imaging system of the present invention obtains retinal and ocular images which can be viewed in real time by on-site or remote video monitors. Furthermore, since the video images are stored and analyzed by computer, the multiple limitations imposed by photographic film technology are avoided. The digital image analysis system employed provides an accurate and relatively easy method for effectively quantifying the retinal vascular response in humans to various physiologic variables, drugs or disease states.

Figure 4:
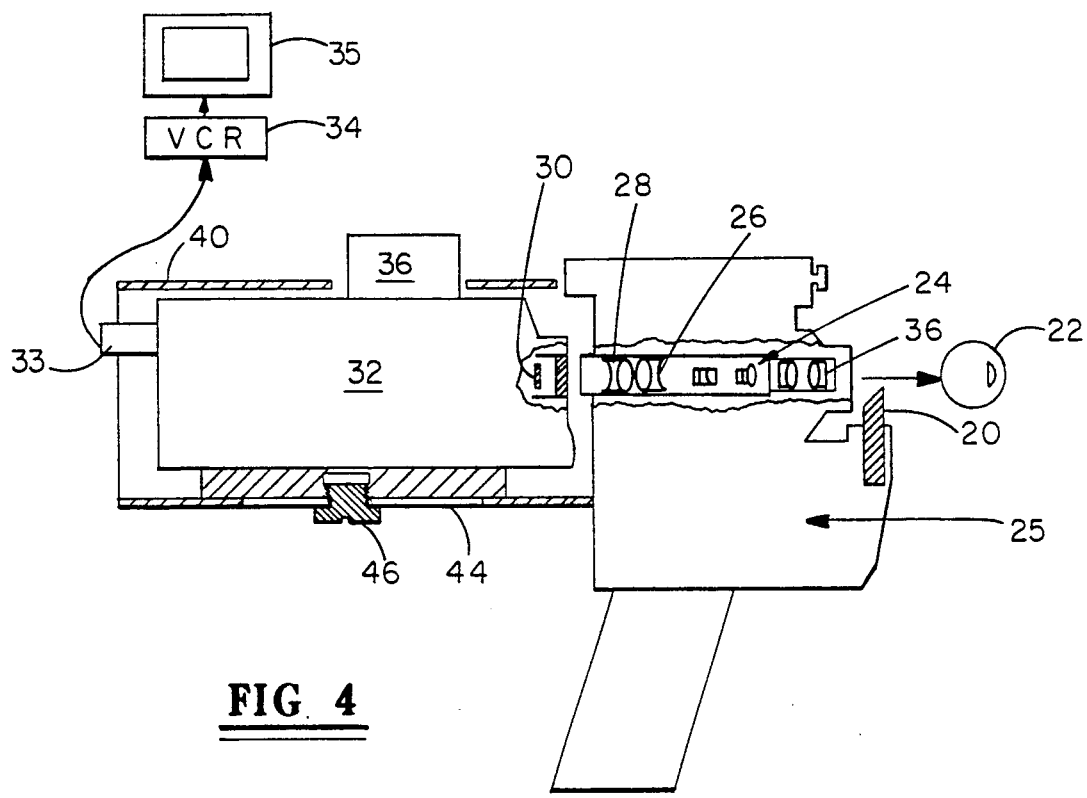
FIG. 4 is a partial schematic representation of a system embodying the present invention.

Referring again to the drawings, the present invention is embodied in a system as partially illustrated in FIG. 4, which includes a light transmitter means 20 for projecting a low intensity light into a dilated eye 22 for illuminating the fundus without damage to the eye. The illumination may be a 10 watt light source. The illumination is made sufficient for an image of the fundus to be transmitted through a focusing lens and an optical system 24. The optical system 24 consists of a series of lens which are conventionally arranged for transmitting the image to a rear relay lens 26. The relay lens 26 is aligned with an infrared cut off filter 28 and an image sensor 30. The image is sensed by a charge coupled device (CCD) 32. The CCD 32 electronically scans the image ar discrete points to obtain digitized signals of the relative image brightness features with horizontal and vertical picture elements. The CCD 32 is connected to an electronic view finder 36 and also has an output plug 33 which is connectable to a Video Cam Recorder 34 and to a Television or Video Monitor 35.

The light transmitter means 20 and the optical system 24 can be obtained by using the light and optics of a Kowa R-2 fundus camera 25 where the lens system is altered to project a properly sized image to the CCD device. A modified Kowa R-2 fundus camera 25 is shown in FIG. 5.

A suitable solid state change coupled device (CCD) 32 can be made from the monochrome camera model 4810 available from Cohu, Inc. located in San Diego, Calif. The model 4810 has solid state elements which obtain high resolution and has high sensitivity and automatic gain control. The resolution includes 754(H)×488(V) picture elements with sensitivity to 0.007 fc/.07Lux. The image area is 8.8×6.6 mm and has a resolution of 565 TV lines horizontally and 350 TV lines vertically. The unit is altered by addition of an infrared cutoff filter 28 to eliminate long wavelength reflections that degrade the image. The adaption of a unit to the Kowa R-2 camera is illustrated in FIG. 5.

The CCD 32 is coupled to an electronic view finder 36 such as the type available from Thompson Comsumer Electronics, Inc. located in Indianapolis, Id. The view finder 36 displays a video image of the fundus images obtained by the CCD 32. Thus, the operator places the input lens 36 in a focus relationship to an eye 22 and can contemporaneously view in real time in the view finder 38 the dynamic functioning of the vessels in the eye 22. The view finder 38 is illustrated in FIG. 5.

Figure 5:
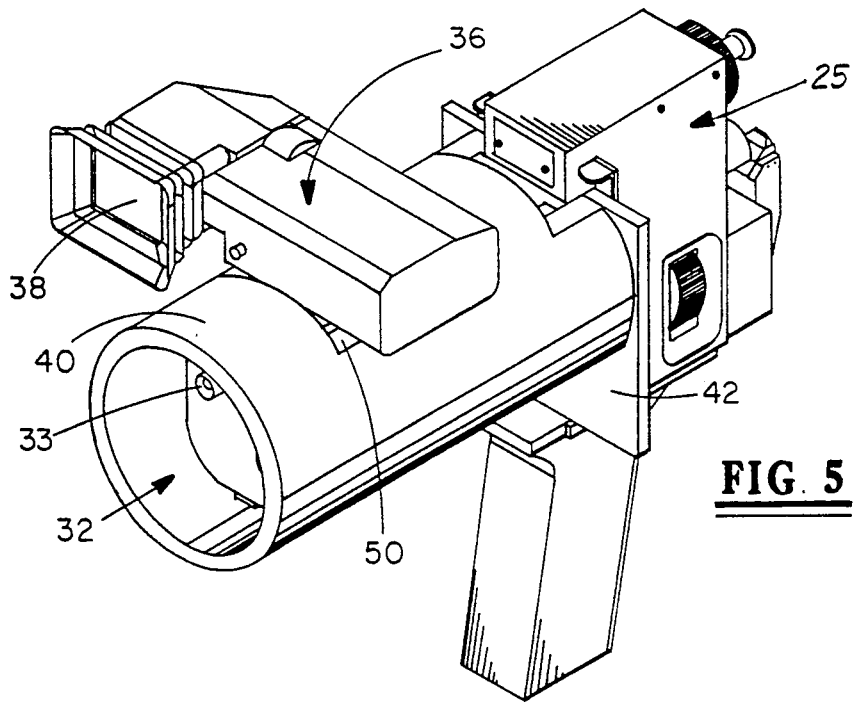
FIG. 5 is an illustration of a commercially producible system which has been modified to practice the present invention.

The physical embodiment illustrated in FIG. 5 utilizes an altered Kowa R-2 unit and an altered CCD device. The CCD device 32 is contained in a tubular housing 40 made of aluminum which is attached to the R-2 unit by a flange coupling 42. A lengthwise extending slot 44 in the housing receives a locking screw 46 on the CCD device so that the lock screws 46 can fix the longitudinal position of the CCD device 32 relative to the optical path. The slot 44 provides for focal length adjustment of the CCD device 32 relative to the optical path. The CCD device 32 has an output plug 33 which is connectable to a recording device such as a VCR and/or CPU for storing the data measurements.

At a diametrically opposed location the housing has an arcuate slot with edge surfaces disposed on a horizontal plane. The slot is sized to receive the view finder assembly 36. At the other end of the housing, a recess 52 is provided to adapt to the housing of the fundus camera.

In operating the system, the operator can utilize a software program for visually displaying a central axis and the two edges of a displayed vessel detected at the time of examination. The operator selects or designates a number of points on the approximate center line of the vessel and the program is used to fit a piecewise linear axis (from point to point) through the designated points from the first to the last point. At each point, the program searches laterally at 90° to the linear axis in both directions for the edge of the vessel. A second order surface is located in a small predefined area and the slope of the second order surface in the center of the area is calculated. The greatest slope in the area is designated the edge point. A curved line is then generated through the two sets of edge points and a curved central axis is located midway between the two edge lines. The length, area, average width and other parameters are then easily calculated.

From the foregoing it can be appreciated that a handheld portable unit is utilizable to obtain a dynamic real time viewing of a fundus together with recording of the data which could be contemporaneously viewed on a TV screen by others, as well as recorded as a dynamic medical record. By use of recordings, changes over a period of time are a matter of comparing the records.

It is also to be understood that the foregoing description of a preferred embodiment of the invention has been presented for purposes of illustration and explanation and is not intended to limit the invention to the precise form disclosed. It is to be appreciated therefore, that various material and structural changes may be made by those skilled in the art without departing from the spirit of the invention.

We claim:

1. A method for evaluating a vessel in an eye for diameter, length and tortusity by sue of a portable eye diagnostic instrument comprising the steps of:
    a) illuminating the fundus of an eye with a low level light,
    b) optically colluminating the image of the fundus to a charge coupling means for developing dynamically occurring data of a fundus image as a function of time, said data including horizontal and vertical picture elements of brightness;
    c) converting the data to a real time visual view using a view finder means coupled to said charge coupling means for real time visual viewing of the fundus image of the eye;
    d) recording the data as a function of time;
    e) isolating a segment of vessel in an image of the fundus;
    f) establishing center points at a number of locations along said segment;
    g) determining maximum slope angles 90° locations in predefined areas at each of said locations for establishing edges of the segment of vessel;
    h) establishing a curvature for the edge surfaces of the segment of vessel utilizing the maximum slope angels; and
    i) establishing a curved center line of the segment of vessel between the curvature for the edge surfaces.

2. The method as set forth in claim 1 and further including the step of separately displaying the data on a video screen for independent viewing of the fundus image of the eye.

* * * * *